United States Patent [19]
Caldarise

[11] Patent Number: 5,681,317
[45] Date of Patent: Oct. 28, 1997

[54] CEMENT DELIVERY SYSTEM AND METHOD

[75] Inventor: Salvatore Caldarise, Hanson, Mass.

[73] Assignee: Johnson & Johnson Professional, Inc., Raynham, Mass.

[21] Appl. No.: 662,398

[22] Filed: Jun. 12, 1996

[51] Int. Cl.[6] .................................................. A61B 17/56
[52] U.S. Cl. .............................. 606/93; 606/92; 604/218
[58] Field of Search ................................ 606/92, 93, 94; 604/187, 191, 218, 231, 226; 156/578

[56] References Cited

U.S. PATENT DOCUMENTS

| | | | |
|---|---|---|---|
| 5,354,285 | 10/1994 | Mazurik et al. | 604/191 |
| 5,409,465 | 4/1995 | Boggs et al. | 60/191 |
| 5,496,284 | 3/1996 | Waldenburg | 604/191 |
| 5,558,136 | 9/1996 | Orrico | 141/23 |

*Primary Examiner*—Michael Buiz
*Assistant Examiner*—David O. Reip

[57] ABSTRACT

The present invention provides a cement delivery system having concentric lumens that terminate in openings at the distal end of the delivery system for providing a selected application of two or more cement types or compositions that vary from the middle of a bone cavity to the circumference of the bone cavity. The invention also provides a method for applying cement into a bone cavity to provide a gradient of materials within the bone cavity from the middle point or center of the bone cavity to the circumference of the cavity.

7 Claims, 3 Drawing Sheets

5,681,317

CEMENT DELIVERY SYSTEM AND METHOD

FIELD OF THE INVENTION

The present invention relates to a cement delivery system and method for applying cement into a bone cavity and for cementing a prosthesis in the cavity.

BACKGROUND OF THE INVENTION

Typically when cementing an orthopedic implant in a bone cavity, cement is delivered to the bone cavity using a single cylinder syringe. If the cement is comprised of more than one material, such materials are typically mixed prior to the extrusion of the cement from the cement applicator. Some cement delivery systems, however, do not mix the materials prior to extrusion but extrude the components separately through a static mixer and then into the bone cavity in a mixed state.

One typical bone cement that has been successfully used is Polymethyl-methacrylate (PMMA). PMMA is believed to fix itself to surfaces with which it comes in contact through a micromechanical interlocking.

Another type of cement that has been used with some success is a bioactive bone cement that incorporates bioactive particles such as glass or other particles that can bond directly to the bone. It is believed that such particles increase the bonding of cement to the bone.

It is also believed, however, that the bioactive bone cement particles can have a negative impact by providing discontinuities in the mantle, thus weakening the cement and its bonding strength to non-biological materials. Accordingly, there are advantages and disadvantages to using PMMA versus PMMA with bioactive particles that must be carefully considered prior to determining which to use and at what concentrations.

Also, preferably, the modulus of elasticity of the cement is preselected for a given application. The modulus of the bone cement is preferably matched to the material to which it is adhering or cementing in order to prevent increased interfacial stresses between the surface of the cement and the surface of the material. It is believed that a stiffer cement would be preferred for the cement adjacent the prothesis or stem whereas a lower modulus of elasticity is preferred for cement adjacent bone tissue. The modulus is typically selected by weighing these competing interests and making a selection accordingly.

It is therefore desirable to provide a bone cement delivery system which can vary the composition of the cement delivered within a bone cavity in relation to the materials adjacent to such cement.

SUMMARY OF THE INVENTION

Accordingly, it is an object of the present invention to provide a cement delivery system that would allow the use of bioactive particles in a controlled manner to maximize their effectiveness. One embodiment of such a cement delivery system may provide bioactive materials in greater concentration adjacent the bone material while in a lesser concentration adjacent the implant material.

It is another object of the invention to provide a cement delivery system that would provide a gradient in the modulus of the elasticity in the cement between the stem and the bone with a greater modulus adjacent the stem and a lesser modulus adjacent the bone.

Therefore, accordingly, the present invention provides a multi-lumen cement delivery system comprised of concentric lumens that are insulated from each other from the insertion of the cement material into each lumen until the cement is extruded from the distal end of the lumens into the bone cavity so that such a gradient or variation in composition within the bone cavity will exist. The diameter of the lumens at the entry points may be adjusted so that the proper proportion of bioactive particles to cement, e.g., PMMA, and/or to various cements having different moduli is provided upon delivery.

DETAILED DESCRIPTION OF THE DRAWINGS

DETAILED DESCRIPTION OF THE INVENTION

Figure 1:
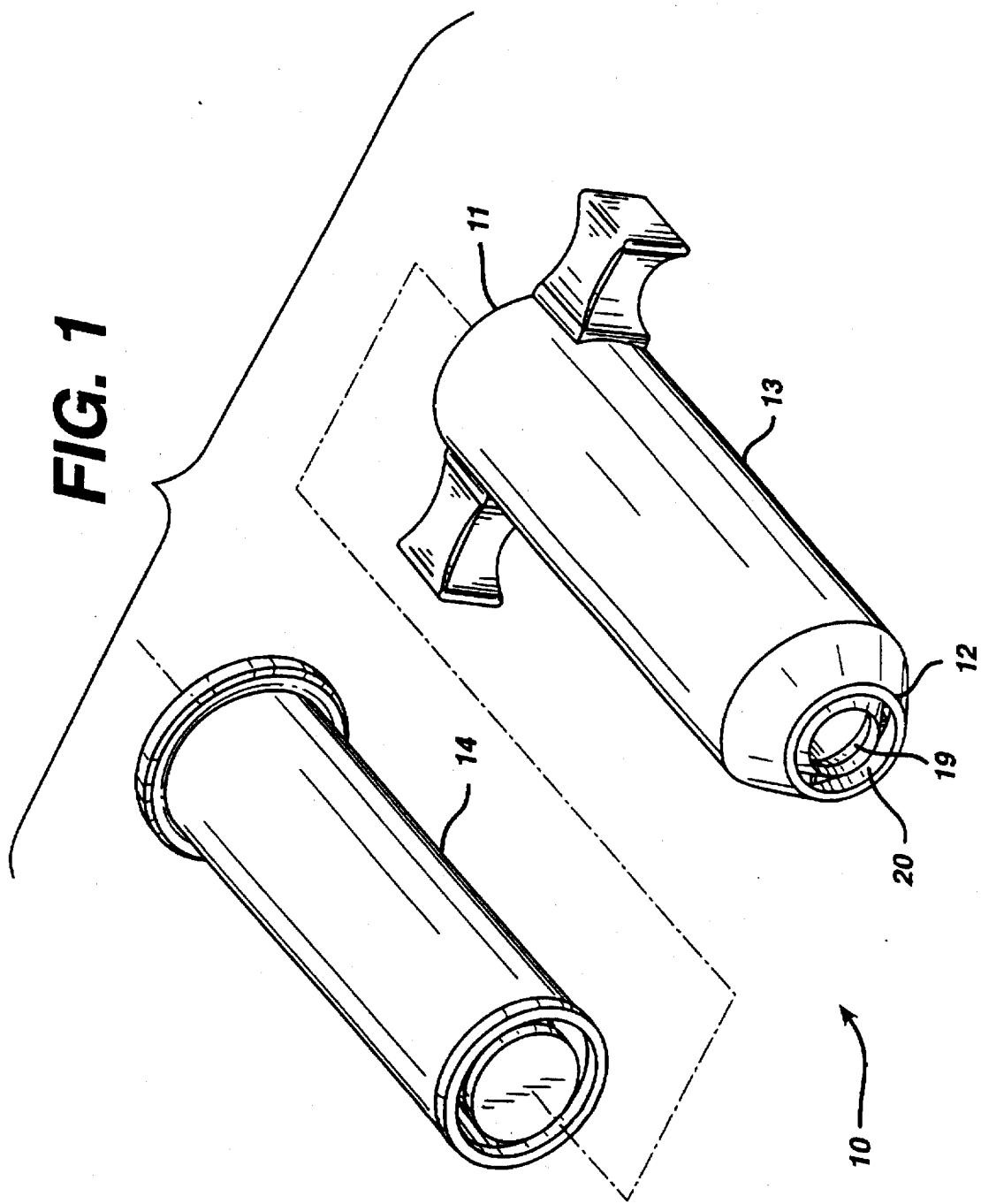
FIG. 1 illustrates an exploded perspective view of the cement delivery system of the present invention.
Figure 2:
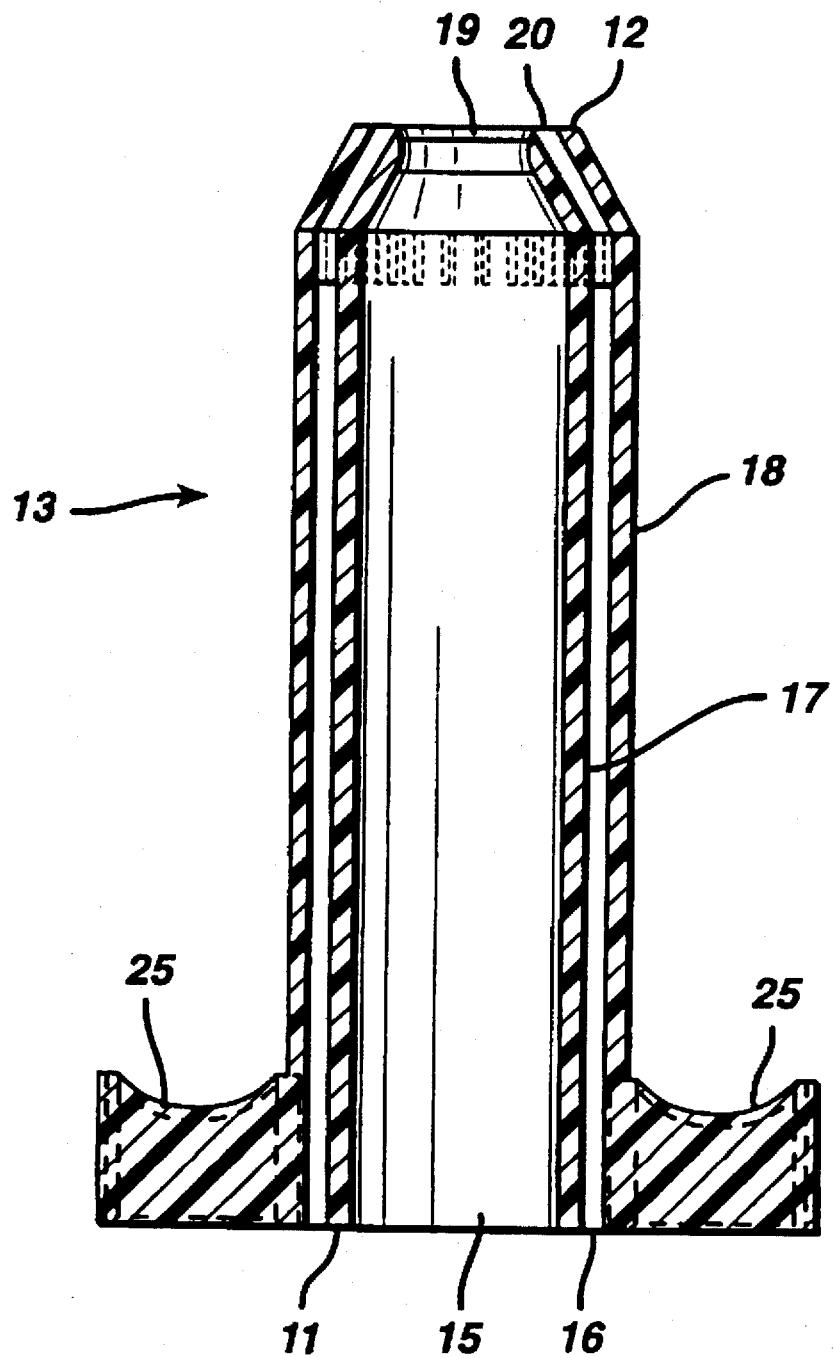
FIG. 2 illustrates a cross-sectional view of the cement holder of the system of FIG. 1.
Figure 3:
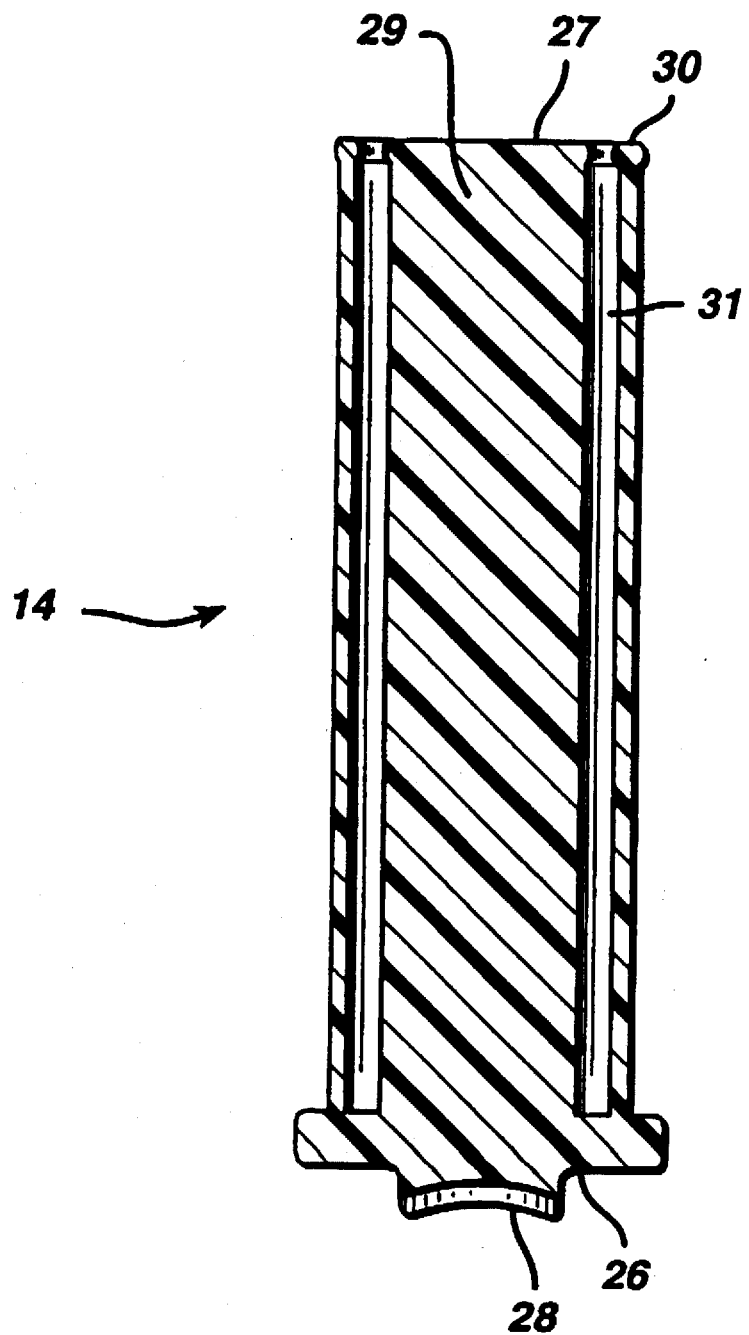
FIG. 3 illustrates a cross-sectional view of the of plunger of the system of FIG. 1.

Referring now to FIG. 1 there is illustrated a cement delivery device 10 of the present invention. The device 10 comprises a cement holding body 13 having a proximal end 11 and a distal end 12. The proximal end 11 includes a plunger device 14 and proximal openings 15, 16 of concentric tubes 17, 18 respectively. The proximal opening 15 to inner tube 17 is of a predetermined diameter to accommodate the desired concentration of material applied through the inner tube 17. The proximal opening 16 to the outer tube 18 is of a diameter and area necessary to have the appropriate concentration of the material extruded from the outer tube 18. The inner tube 17 and outer tube 18 extend to the distal end 12 of the cement delivery device 10 terminating in distal openings 19, 20 of the inner tube and outer tube 17, 18, respectively. The diameters of the openings 19, 20 are preferably a function of the viscosities of the material to be delivered and desired ratios of the material so that each material is extruded at a predetermined rate in relation to the other material(s). The cement holding device 13 further comprises finger grips 25 to for holding the device while extruding cement.

The plunger 14 comprises a proximal end 26 and a distal end 27. An extruding button 28 is located at the proximal end 26 of the plunger 14. The plunger 14 further comprises an inner block 29, an outer block 30 and a circumferential opening 31 extending between the blocks 29, 30 extending from the distal end 27 to the proximal end 26 where the blocks 29,30 are joined.

In use, a first cement is inserted into tube 17 through opening 15 and a second cement is inserted into tube 18 through opening 16. The distal end 26 of the plunger 14 is placed within the cement holder 13 with the block 29 extending into the outer tube 18 and the block 30 extending into the inner tube 17. The cylindrical opening 31 fits over the outer wall of the inner tube 17.

The distal end 19 of the cement holding body 13 is inserted into a prepared cavity of a femoral bone. The plunger 14 is advanced distally by pressing the button 28 while grasping the finger grips 25 of the cement holder 13 thereby extruding cement into the prepared cavity.

The cement inserted into opening 16 is preferably comprised of polymethylmethacrylate cement and bioactive particles. The bioactive particles are inserted in a polymethylmethacrylate mixture, through the outer tube 18 of the cement delivery system while polymethylmethacrylate without the particles is inserted through the inner tube 17 of the cement delivery system 10. The delivery system thus provides a greater concentration of bioactive particles adjacent the bone with a greater concentration of polymethylmethacrylate cement adjacent the stem of a femoral component inserted into the femoral cavity.

In preferred embodiments and the cement delivery system is used to prepare a femoral or tibial bone for receipt of cement to implant a hip or knee prothesis.

Although, this invention is described in connection with a particular embodiment numerous modifications may be made without departing from the scope of the invention claimed herein. For example, numerous lumens may be provided in a concentric arrangement while a gradient of modulus of elasticity of cement is provided from the center of the bone cavity to the inner circumference of the bone cavity to provide a transition from a high modulus to a lower modulus of elasticity.

For example three different concentrations of PMMA and polybutylmethylmethacrylate (butyl methacrylate beads in a methylmethacrylate matrix) (PBMMA) may be used. For example 100% PMMA having a modulus of elasticity of about 2.10 Gigapascals (Gpa) would be inserted into an innermost tube while 50% PMMA and 50% PBMMA having a modulus elasticity of 1.19 Gpa would be inserted into the middle tube and 100% PBMMA having a modulus of elasticity of 0.27 Gpa would be inserted into the outermost tube.

Thus the greater modulus of elasticity material would tend to locate towards the middle of the cavity and therefore adjacent the implant, the lowest modulus of elasticity material would tend to locate towards the outside of the cavity and therefore adjacent the bone and the middle of the cavity wall tend to have a transitional modulus of elasticity thereby allowing a smooth transition from a high modulus to a low modulus without a steep gradient in elastic modulus.

I claim:

1. A cement delivery system comprising:

a distal portion coupled to a plurality of concentric tubes extending to a distal end of the cement delivery system, each of said plurality of tubes terminating at said distal end in an opening concentric with each said opening of the other of said plurality of tubes; and a cement plunger located at a proximal end of said cement delivery system, said plunger comprising a plurality of concentric plunger element fixed at a proximal end, said plurality of plunger elements corresponding to said plurality of concentric tubes such that said cement plunger is moveable in a proximal to distal direction within said concentric tubes to extrude cement through said tubes to said distal end of said tubes.

2. The cement delivery system of claim 1, further comprising a plurality of cement compositions having different moduli of elasticity.

3. The cement delivery system of claim 1, further comprising a plurality of cement compositions including a cement composition comprised of a mixture of cement and bioactive particles.

4. The cement delivery system of claim 2, wherein each of said plurality of cement compositions is extruded substantially separately from the other of said plurality of cement compositions at said distal end of the cement delivery system.

5. A method of delivering cement to a bone cavity comprising the steps of:

providing a cement delivery device comprising:

a plurality of concentric tubes having a proximal end and a distal end, said tubes comprising openings at the proximal end of said tubes for receiving cement; said tubes terminating in concentric distal openings at the distal end of said delivery device; and a cement plunger located at a proximal end of said cement delivery system moveable in a proximal to distal direction within said concentric tubes to extrude cement through said tubes to said distal end of said tubes;

providing a plurality of cement compositions;

inserting a first selected cement composition in a first of said tubes;

inserting a second selected cement composition in a second of said tubes;

placing the distal end of said tubes within a bone cavity prepared to receive a prosthetic implant;

advancing said plunger of said delivery device distally to extrude said first and second cement compositions out of the distal end of the tubes into the bone cavity; and inserting a prosthetic device to be fixed to the bone, into the bone cavity.

6. The method of claim 5, wherein said first tube comprises a central lumen and wherein said second tube comprises concentric tube around said first tube;

further comprising the steps of selecting said first selected cement from a group of cements having a modulus of elasticity from a first desired range of moduli of elasticity; and selecting said second selected cement from a group of cements having a modulus of elasticity from a second desired range of moduli of elasticity;

wherein said first selected cement has a greater modulus of elasticity than said second selected cement.

7. The method of claim 5 wherein said first tube comprises a central lumen and wherein said second tube comprises concentric tube around said first tube;

wherein said second selected cement comprises a mixture of a cement and bioactive particles.

* * * * *